United States Patent [19]

Perozzi et al.

[11] Patent Number: 5,174,922
[45] Date of Patent: Dec. 29, 1992

[54] REDUCING COPPER CORROSIVENESS OF ORGANIC POLYSULFIDES

[75] Inventors: Edmund F. Perozzi, Crestwood; Andrew G. Papay, Manchester, both of Mo.

[73] Assignee: Ethyl Petroleum Additives, Inc., St. Louis, Mo.

[21] Appl. No.: 435,592

[22] Filed: Nov. 13, 1989

[51] Int. Cl.$^5$ ............... C07C 321/12; C07C 321/14; C07C 321/20

[52] U.S. Cl. ............... 252/395; 252/389.61; 252/389.62; 422/7; 568/21

[58] Field of Search ............... 252/389.61, 389.62, 252/395; 422/7; 568/21

[56] References Cited

U.S. PATENT DOCUMENTS

| | | | |
|---|---|---|---|
| 2,218,997 | 10/1940 | Wasson | 568/21 |
| 2,521,870 | 9/1950 | Proell | 568/21 |
| 2,708,199 | 5/1955 | Eby | 260/327 |
| 3,471,404 | 10/1969 | Myers | 252/45 |
| 4,645,610 | 2/1987 | Born et al. | 568/21 |
| 4,827,040 | 5/1989 | Labat et al. | 568/21 |
| 4,954,274 | 9/1990 | Zaweski et al. | 252/45 |

FOREIGN PATENT DOCUMENTS 59-10559  1/1984  Japan .

Primary Examiner—Deborah L. Kyle
Assistant Examiner—Valerie D. Fee
Attorney, Agent, or Firm—John F. Sieberth; Doris M. Thompson

[57] ABSTRACT

The invention provides a process of reducing the copper corrosiveness of dihydrocarbyl polysulfides by treating them with an alkali metal-containing or alkaline earth metal-containing substance capable of dissolving elemental sulfur (e.g., sodium hydroxide, sodium sulfide, etc.). The process is conducted in a liquid reaction medium composed of a mixture of water and at least one water-soluble alcohol. Experiments have shown that it is possible by use of this process to reduce the copper corrosiveness to a level below that exhibited by a product formed by treating the same initial dihydrocarbyl polysulfide in the same way but in a liquid medium composed solely of water.

33 Claims, No Drawings

REDUCING COPPER CORROSIVENESS OF ORGANIC POLYSULFIDES

TECHNICAL FIELD

This invention relates to reducing the copper corrosiveness of dihydrocarbyl polysulfides.

BACKGROUND

Japan Kokai 59-10559 describes a process wherein dialkyl polysulfide is treated with an aqueous solution of sodium sulfide at 30°–80° C. for 1–5 hours. The treated product is indicated to have reduced copper corrosiveness, and the applicants in that laid open application express their belief that the reduction in copper corrosiveness is due to a chemical reaction whereby dialkyl tetrasulfide and dialkyl pentasulfide are converted into a less corrosive dialkyl trisulfide.

U.S. Pat. No. 4,827,040 describes a process wherein dialkyl polysulfides are treated with a variety of substances capable of dissolving elemental sulfur, such as alkali metal, alkaline earth and ammoniacal bases, hydrosulfides, alkali metal sulfites, caustic soda, caustic potash, lime, sulfides of sodium, potassium, calcium or ammonium, etc. The treatments when using such inorganic treating agents are conducted in aqueous solutions, and in the process the dialkyl polysulfides are transformed into dialkyl polysulfides having a reduced sulfur content. The most desired product of this process, according to the patentees, is dimethyl disulfide because of its usefulness as a solvent for sulfur in cleaning natural gas conduits.

THE INVENTION

This invention involves, inter alia, the discovery that it is possible to reduce the copper corrosiveness of dialkyl polysulfide to even lower levels than achieved by use of the aqueous solutions of $Na_2S$ referred to in Japan Kokai 59-10559. Moreover this invention involves the further discovery that substances capable of dissolving elemental sulfur—i.e., alkali metal containing and alkaline earth metal-containing substances of the type referred to in U.S. Pat. No. 4,827,040—can be used to reduce the copper corrosiveness of dialkyl polysulfides and that by modifying the solvent system, even lower levels of copper corrosiveness can be achieved. And additionally, the copper corrosiveness of dihydrocarbyl polysulfides other than dialkyl polysulfides can be effectively reduced by the practice of this invention.

In accordance with one of its embodiments, this invention provides a process of reducing the copper corrosiveness of dihydrocarbyl polysulfide that is corrosive toward copper which comprises treating such dihydrocarbyl polysulfide with an alkali metal-containing or alkaline earth metal-containing substance capable of dissolving elemental sulfur, such treatment being conducted in a liquid reaction medium composed of a mixture of water and at least one water-soluble alcohol.

With reference to prior processes such as are described in Japan Kokai 59-10559 and U.S. Pat. No. 4,827,040, this invention provides in a process of treating dialkyl polysulfide with an alkaline inorganic substance capable of dissolving elemental sulfur, the improvement which comprises conducting such treatment in a liquid reaction medium comprising water and at least one alcohol such that the resultant dialkyl polysulfide exhibits reduced copper corrosiveness. Indeed, as will be seen in the examples hereinafter, it is possible by use of this process to reduce the copper corrosiveness to a level below that exhibited by a product formed by treating the same initial dialkyl polysulfide in the same way but in a liquid medium composed solely of water.

Still another embodiment of this invention is a dihydrocarbyl polysulfide (most preferably dialkyl polysulfide) formed by a treatment process of this invention, such product being characterized by exhibiting less copper corrosiveness than a product formed from the same initial dihydrocarbyl polysulfide using the same treatment process but in the absence of the alcohol or mixture of alcohols.

These and other embodiments, features and advantages of this invention will be still further apparent from the ensuing description and appended claims.

This invention is deemed applicable to any dihydrocarbyl polysulfide having the adverse property of exhibiting excessive corrosiveness towards copper. A convenient test procedure for use in measuring copper corrosiveness is as follows: A copper coupon approximately 70×15 mm and about 1.25 mm in thickness is cleaned by use of steel wool (0000 grade), washed with heptane, and then with acetone, dried, and weighed to the nearest 0.1 mg. The cleaned coupon is placed in a test tube and covered completely with the composition to be tested, and the system is heated to 121° C., by means of an oil bath maintained at this temperature. After holding the system at 121° C. for three hours, the copper coupon is removed from the test tube, rinsed with heptane and then with acetone. The dried coupon is then rubbed with a paper towel moistened with acetone to remove any surface flakes formed by copper corrosion. The coupon is then air-dried and weighed to the nearest 0.1 mg. The difference in weight as between the initial copper coupon and the coupon after the test represents the extent to which the copper was corroded under the test conditions. Therefore the smaller the weight difference, the less the copper corrosion.

This invention is thus applicable to individual dihydrocarbyl polysulfides and mixtures of two or more dihydrocarbyl polysulfides wherein in either case at least a portion of polysulfide moiety contains, at least four sulfur atoms and wherein the hydrocarbyl groups are alkyl, alkenyl, cycloalkyl, cycloalkylalkyl, aryl, aralkyl, cycloalkenyl, or the like. Such hydrocarbyl groups each can contain any number of carbon atoms, e.g., 100 or more, preferably 50 or less, most preferably up to about 18 carbon atoms, so long as the compound or mixture of compounds exhibits corrosiveness toward copper as seen for example in the above copper corrosion test. Especially preferred dihydrocarbyl polysulfides are dialkyl polysulfides containing 3 to about 18 carbon atoms in each alkyl group, most especially where the polysulfide product being treated pursuant to this invention includes at least dialkyl tetrasulfide and/or dialkyl pentasulfide.

The hydrocarbyl groups of the polysulfides used in the process can be substituted by innocuous substituents, i.e., substituents that do not interfere with or prevent the reduction in copper corrosiveness made possible by the practice of this invention. For example, the hydrocarbyl substituents of the dihydrocarbyl polysulfides may include ether oxygen atoms, thioether sulfur atoms, nitrogen atoms, etc. Thus the polysulfides used in the process of this invention include alkoxyalkyl and (polyalkoxy)alkyl-substituted polysulfides, alkylthioalkyl-substituted polysulfides, aryloxyalkyl polysulfides, dialkylaminoalkyl polysulfides, diarylaminoalkyl polysulfides, and in general, any polysulfide of the formula R—$S_n$—R' wherein the average value of n is above 3, (preferably 3.5 or above). Thus, the average value for n may vary considerably, but usually is in the range of about 3.5 to about 12 or more. In this formula, each of R and R' is independently, any organic group (cyclic or non-cyclic) containing carbon and hydrogen, and optionally one or more oxygen, sulfur, nitrogen, and/or halogen atoms, all with the proviso that each organic group is bonded to the polysulfide moiety by a carbon-sulfur bond and the compound is corrosive toward copper and is amenable to treatment pursuant to this invention.

The alkali metal-containing substance or alkaline earth metal-containing substance used in the process of this invention is any such compound or mixture of such compounds that is capable of dissolving elemental sulfur. Such compounds, many of which are referred to in U.S. Pat. No. 4,827,040, include alkali metal oxides, alkali metal hydroxides, alkali metal hydrosulfides, alkali metal mercaptides, and the corresponding alkaline earth metal compounds. Mixtures of two or more such alkali metal-containing compounds or of two or more such alkaline earth metal-containing compounds or of one or more such alkali metal-containing compound(s) with one or more such alkaline earth metal-containing compound(s) can be used. A few examples of such compounds are LiOH, NaOH, KOH, $Na_2O$, $K_2O$, CsOH, MgO, CaO, $Mg(OH)_2$, $Sr(OH)_2$, BaO, $Ba(OH)_2$, NaSH, $NaSCH_3$, $NaSC_2H_5$, $NaSC_6H_5$, KSH, $Na_2SO_3$, $K_2SO_3$, $Na_2S$, $K_2S$, and the like. As is well known, the foregoing oxides are converted into hydroxides in the presence of water and thus when using such oxides the reaction medium in which the treatment occurs will contain hydroxide ions formed by the interaction of the oxide with water. Use of sodium oxide, potassium oxide, sodium hydroxide or potassium hydroxide, or any combination of two or more of these constitutes a preferred embodiment of this invention. Another preferred embodiment involves the use of sodium sulfide or potassium sulfide or a mixture of the two as the treating agent.

The amount of treating agent used in the process can be widely varied. All that is required is to use a sufficient amount of the treating agent to cause the resultant treated dihydrocarbyl polysulfide to have reduced copper corrosiveness as compared to the same initial dihydrocarbyl polysulfide, not subjected to the treatment process of this invention. The optimum quantities can thus be readily determined in any given situation by the simple expedient of performing a few tests. In most cases, the treatment process will involve use of at least about 15 parts by weight of the treating agent per 100 parts by weight of the initial dihydrocarbyl polysulfide being treated. Amounts of treating agent in the range of about 25 to about 300 parts by weight per 100 parts by weight of dihydrocarbyl polysulfide being treated are typical. However, departures from these ranges are permissible whenever deemed appropriate or desirable, and are thus within the ambit of this invention.

It is possible to use any monohydric or polyhydric alcohol in forming the mixed solvent systems used in the practice of this invention. Thus use may be made of alkanols, alkenols, alkynols, glycols(diols), triols and other polyols, polyether alcohols and the like. For best results the alcohol or mixture of alcohols used in the solvent system should be at least partially soluble in water at the principal temperature(s) to be used in the treatment process. Alcohols that are either miscible or at least highly soluble in water, such as methanol, ethanol, propanol, isopropanol, butanol, isobutanol, sec-butanol, tert-butanol, allyl alcohol, ethylene glycol, erythritol, pentaerythritol, trimethylolpropane, anhydroenneaheptitol, 1,2,4-butanetriol, 1,2,6-hexanetriol, threitol, ribitol, arabinitol, xylitol, allitol, sorbitol, mannitol, altritol, iditol, and the like, are preferred. Alcohols having relatively low solubility in water such as the pentanols, hexanols and the like are best used in combination with another alcohol or mixture of alcohols that has or have high water solubility to achieve mutual solubilization. Alternatively, the alcohol(s) having relatively low water solubility may be used in conjunction with other solvents having high water solubility, such as acetone, tetrahydrofuran, etc.

Generally speaking, the alcohols used are desirably those which have a solubility in water of at least about 5% (and more preferably at least about 25%) by weight measured at 30° C.

As noted above, the process of this invention is conducted in a liquid reaction medium composed at least predominantly of one or more alcohols and water. The relative proportions as between the alcohol(s) and the water may be varied widely provided the mixture provides sufficient solubility for the treating agent and the dihydrocarbyl polysulfides to enable the treatment process to proceed efficiently and effectively. Thus generally speaking the liquid reaction medium will contain from about 5 to about 95 volume percent of water with the balance being one or more alcohols (together with mutual solubilizing co-solvent such as acetone or tetrahydrofuran, if used).

Treatment temperatures generally fall in the range of about 35° to about 150° C., and preferably in the range of about 50° to about 90° C.

The practice and advantages of this invention are further illustrated by the following examples, which are not to be construed as limiting the scope of this invention.

EXAMPLE 1

Synthesis of Di-tert-Butyl Polysulfide

Oleylamine (1.3 g) was added to 416 g (13 mols) of sulfur. To this was added dropwise with stirring over 4.25 hours a total of 900 g (10 moles, 1125 mL) of tert-butyl mercaptan at 20°–30° C. It was noticed that when 325 mL of the mercaptan had been added, the rate of hydrogen sulfide evolution had slowed. An additional 1.3 g of oleylamine was added at this point. After addition of the mercaptan was complete, the temperature was raised to 40° C. for 0.5 hr. The temperature was raised to 70° C. and kept at this temperature for 1.5 hours. Some refluxing was noticed. High vacuum was applied and the temperature was raised to 100° C. for 40 minutes. Filtration removed fine black precipitate. The clear, yellow mobile liquid product weighed 982.7 g. (85.7% yield).

EXAMPLE 2

Treatment with Sodium Sulfide in Water-Alcohol Medium

To 93.8 g of sodium sulfide dissolved in 300 mL of water was added 300 mL of isopropanol. To the resulting two-phase system was added 100 g of di-tert-butyl polysulfide prepared as in Example 1. Heat was applied and the mixture turned dark red-brown in color and became a single phase system. The mixture was heated to reflux for about 1 hour. The lower layer was separated by extraction and the upper organic layer was treated in a separatory funnel with 100 mL. of water. The top oily phase was separated from the lower aqueous layer and the oily phase was subjected to rotary evaporation yielding 58.06 g of di-tert-butyl polysulfide product.

EXAMPLE 3 (COMPARATIVE)

Treatment with Sodium Sulfide in Water

To a solution composed of 93.8 g of sodium sulfide dissolved in 600 mL of water was added 100 g of di-tert-butyl polysulfide prepared as in Example 1. The mixture was heated to 81° C. and held at this temperature for approximately 1 hour. The organic phase was recovered by means of a separatory funnel and washed with 100 mL of water. The resulting organic phase (the bottom layer) was separated and subjected to rotary evaporation to remove small amounts of residual water. A total of 83.79 g of di-tert-butyl polysulfide was obtained. This was again filtered to remove a few remaining drops of water, thereby yielding 71.9 g of product.

Samples of the di-tert-butyl polysulfides from Examples 1, 2, and 3 were subjected to the standard copper corrosion test described hereinabove (3 hours at 121° C.). The loss in weight (expressed in milligrams) of the copper coupons used in these tests is shown in Table I.

TABLE I

| Di-tert-butyl polysulfide used | Copper Corrosion Tests | |
|---|---|---|
| | Copper Weight Loss, mg | Corrosion Reduction % |
| Example 1 (untreated) | 615.5 | — |
| Example 2 (treated per this invention) | 9.0 | 98.5 |
| Example 3 (treated per prior art) | 296.6 | 51.8 |

EXAMPLE 4

Treatment with Sodium Hydroxide in Water-Alcohol Medium

To 66.67 g of sodium hydroxide dissolved in 300 mL of water was added 300 mL of isopropanol. To the resulting two-phase system was added 100 g of di-tert-butyl polysulfide prepared as in Example 1. Heat was applied and the mixture was heated to reflux for about 1 hour. The organic phase was subjected to rotary evaporation to remove most of the solvent. The product was then allowed to stand whereby two phases developed. The bottom aqueous phase was discarded and the organic phase was washed with 100 mL of water. Since an emulsion formed, an additional 50 mL of water containing a small amount of sodium chloride was added. After another phase separation, the organic phase was again subjected to rotary evaporation thereby yielding 78.55 g of di-tert-butyl polysulfide product which was light yellow in color.

EXAMPLE 5 (COMPARATIVE)

Treatment with Sodium Hydroxide in Water

To a solution composed of 66.67 g of sodium hydroxide dissolved in 600 mL of water was added 100 g of di-tert-butyl polysulfide prepared as in Example 1. The mixture was heated to 80° C. and held at this temperature for approximately 1 hour. The organic phase was recovered by means of a separatory funnel and washed with 100 mL of water. The resulting organic phase (the bottom layer) was separated and subjected to rotary evaporation to remove small amounts of residual water. A total of 98.21 g of a hazy di-tert-butyl polysulfide product was obtained. This was filtered to remove residual water, thereby yielding 93.88 g of product.

Samples of the di-tert-butyl polysulfides from Examples 1, 4, and 5 were subjected to the above standard copper corrosion test (3 hours at 121° C.). Table II summarizes the results of these tests.

TABLE II

| Di-tert-butyl polysulfide used | Copper Corrosion Tests | |
|---|---|---|
| | Copper Weight Loss, mg | Corrosion Reduction % |
| Example 1 (untreated) | 502.6 | — |
| Example 4 (treated per this invention) | 23.8 | 95.3 |
| Example 5 (treated per prior art) | 491.2 | 2.3 |

EXAMPLE 6

Synthesis of Di-tert-Butyl Polysulfide

Into a flask was placed 106.6 g of sulfur (3.33 mol) and 200.0 g (250 mL, 2.22 mol) of tert-butyl mercaptan. To the stirring mixture under a nitrogen atmosphere was cautiously added few drops of triethylamine. Vigorous gas evolution occurred and the temperature rose to 35° C. When the vigorous reaction subsided, the reaction mixture was heated to 40° C. for 1 hour. Additional triethylamine was added to a total of 2.22 g, (0.022 mol, 3.06 mL). The sulfur dissolved. The material was heated at 85° C. for 1 hour and cooled to room temperature. The product was washed with three 100 mL portions of 10% sodium hydroxide solution and two 100 mL portions of water. The product was dried by heating at 100° C. under a high vacuum using a rotary evaporator. The product was filtered to yield 234.0 g (87.4%) of a light yellow mobile oil with a trace of mercaptan odor.

EXAMPLE 7

Treatment with Sodium Sulfide in Water-Alcohol Medium

Into a flask were charged 100 g of di-tert-butyl polysulfide produced as in Example 6, 93.8 g of sodium sulfide ($Na_2S \cdot 9H_2O$) in 300 mL of water, and 300 mL of isopropanol. The mixture was heated to reflux for 0.5 hour. The organic oil was removed and washed with 100 mL of water and dried at 100° C. under high vacuum on a rotary evaporator to yield 53.5 g of product.

Samples of the products from Examples 6 and 7 were subjected to analysis to determine the mole percentages of the various di-tert-butyl polysulfides in the respective products. In addition, samples of the products from Examples 6 and 7 were subjected to the above copper corrosion test (3 hours at 121° C). The results of these analyses and corrosion tests are summarized in Tables III and IV, respectively.

TABLE III

Mole Percentage Distribution of Components in Untreated and Treated Dihydrocarbyl Polysulfide Mixtures, R—S$_n$—R

| Value of n | Product of Example 6 | Product of Example 7 |
|---|---|---|
| 2 | none | 9.3 |
| 3 | 15.4 | 59.6 |
| 4 | 35.5 | 25.2 |
| 5 | 23.1 | 3.8 |
| 6 | 15.4 | 1.4 |
| 7 | 7.4 | 0.5 |
| 8 | 2.3 | 0.2 |
| 9 | 0.6 | 0.1 |
| 10 | 0.2 | none |

TABLE IV

Copper Corrosion Tests

| Di-tert-butyl polysulfide used | Copper Weight Loss, mg | Corrosion Reduction % |
|---|---|---|
| Example 6 (untreated) | 877.5 | — |
| Example 7 (treated per this invention) | 59.1 | 93.3 |

The treated products of this invention are useful as extreme pressure additives for lubricating oils. They also exhibit antioxidant and antiwear properties in lubricants.

While this invention has been discussed with reference to treatment of dihydrocarbyl polysulfides, it is contemplated that similar results can be achieved by applying the process of this invention to other organopolysulfide materials such as sulfurized monoolefins or polyolefins, (e.g. sulfurized isobutylene), sulfurized aliphatic esters of olefinic mono- or dicarboxylic acids, and the like.

This invention is susceptible to considerable variation in its practice within the spirit and scope of the appended claims, the forms hereinbefore described constituting preferred embodiments thereof.

What is claimed is:

1. A process of reducing the copper corrosiveness of dihydrocarbyl polysulfide that is corrosive toward copper which comprises treating such dihydrocarbyl polysulfide with an alkali metal-containing or alkaline earth metal-containing substance capable of dissolving elemental sulfur, such treatment being effected in a liquid reaction medium composed of a mixture of water and at least one water-soluble alcohol, whereby the treated dihydrocarbyl polysulfide is less corrosive toward copper.

2. A process as claimed in claim 1 wherein the dihydrocarbyl polysulfide subjected to such treatment comprises at least dialkyl trisulfide, dialkyl tetrasulfide and dialkyl pentasulfide.

3. A process as claimed in claim 1 wherein the dihydrocarbyl polysulfide subjected to such treatment is dialkyl polysulfide containing at least 3 but no more than about 18 carbon atoms in each alkyl group.

4. A process as claimed in claim 1 wherein said substance used in such treatment consists essentially of alkali metal oxide or hydroxide, or both.

5. A process as claimed in claim 1 wherein said substance used in such treatment consists essentially of alkali metal sulfide.

6. A process as claimed in claim 1 wherein said substance used in such treatment consists essentially of sodium oxide, sodium hydroxide, potassium oxide, or potassium hydroxide, or a mixture of any two or more of the foregoing.

7. A process as claimed in claim 1 wherein the said substance used in such treatment is predominantly or entirely sodium hydroxide.

8. A process as claimed in claim 1 wherein said substance used in such treatment consists essentially of sodium sulfide or potassium sulfide, or a mixture of the foregoing.

9. A process as claimed in claim 1 wherein the said substance used in such treatment is predominantly or entirely sodium sulfide.

10. A process as claimed in claim 1 wherein the alcohol used in such reaction medium is predominantly or entirely an alkanol containing up to about 4 carbon atoms in the molecule or a mixture of any two or more of such alkanols.

11. A process as claimed in claim 10 wherein such alkanol consists essentially of isopropanol.

12. A process as claimed in claim 1 wherein the process is conducted at treatment temperatures which fall at least predominantly in the range of about 50° to about 90° C.

13. A process as claimed in claim 1 wherein the dihydrocarbyl polysulfide subjected to such treatment comprises at least dialkyl trisulfide, dialkyl tetrasulfide and dialkyl pentasulfide and wherein said substance used in such treatment consists essentially of alkali metal oxide or hydroxide, or both.

14. A process as claimed in claim 13 wherein said substance used in such treatment consists essentially of sodium oxide, sodium hydroxide, potassium oxide, or potassium hydroxide, or a mixture of any two or more of the foregoing.

15. A process as claimed in claim 13 wherein the said substance used in such treatment is predominantly or entirely sodium hydroxide.

16. A process as claimed in claim 13 wherein the alcohol used in such reaction medium is predominantly or entirely an alkanol containing up to about 4 carbon atoms in the molecule or a mixture of any two or more of such alkanols.

17. A process as claimed in claim 16 wherein such alkanol consists essentially of isopropanol.

18. A process as claimed in claim 1 wherein the dihydrocarbyl polysulfide subjected to such treatment comprises at least dialkyl trisulfide, dialkyl tetrasulfide and dialkyl pentasulfide and wherein said substance used in such treatment consists essentially of alkali metal sulfide.

19. A process as claimed in claim 18 wherein said substance used in such treatment consists essentially of sodium sulfide or potassium sulfide, or a mixture of the foregoing.

20. A process as claimed in claim 18 wherein the said substance used in such treatment is predominantly or entirely sodium sulfide.

21. A process as claimed in claim 18 wherein the alcohol used in such reaction medium is predominantly or entirely an alkanol containing up to about 4 carbon atoms in the molecule or a mixture of any two or more of such alkanols.

22. A process as claimed in claim 21 wherein such alcohol consists essentially of isopropanol.

23. A process as claimed in claim 1 wherein the alcohol or mixture of alcohols is soluble in water to the extent of at least about 5 percent by weight measured at 30° C.

24. A process as claimed in claim 1 wherein the alcohol or mixture of alcohols is soluble in water to the extent of at least about 25 percent by weight measured at 30° C.

25. In a process of treating dialkyl polysulfide with an alkaline inorganic substance capable of dissolving elemental sulfur, the improvement which comprises conducting such treatment in a liquid reaction medium comprising water and a water-soluble alkanol such that the resultant dialkyl polysulfide exhibits reduced copper corrosiveness.

26. The improvement of claim 25 wherein said alkaline inorganic substance is an alkali metal oxide, alkali metal hydroxide, alkali metal sulfide, or any mixture of two or more of the foregoing, and wherein the alkanol is an alkanol or a mixture of alkanols having from 1 to 4 carbon atoms in the molecule.

27. The improvement of claim 25 wherein said alkaline inorganic substance is sodium oxide, potassium oxide, sodium hydroxide, potassium hydroxide, sodium sulfide, potassium sulfide, or any mixture of two or more of the foregoing, and wherein the alkanol is an alkanol or a mixture of alkanols having from 1 to 4 carbon atoms in the molecule.

28. A product formed by the treatment process of claim 1, said product being characterized by exhibiting less copper corrosiveness than a product formed from the same initial dihydrocarbyl polysulfide using the same treatment process but in the absence of the alcohol.

29. A product as claimed in claim 28 wherein the hydrocarbyl groups are alkyl groups.

30. A process as claimed in claim 1 wherein the dihydrocarbyl polysulfide subjected to such treatment is a polysulfide of the formula $R-S_n-R'$ wherein each of R and R' is, independently, a hydrocarbyl substituent which includes optionally one or more of ether oxygen atoms, thioether sulfur atoms, or nitrogen atoms; wherein each said substituent is bonded to the polysulfide moiety by a carbon-sulfur bond; and wherein the average value of n is above 3.

31. A process as claimed in claim 30 wherein the average value for n is in the range of about 3.5 to about 12.

32. A process as claimed in claim 31 wherein said substance used in such treatment consists essentially of sodium oxide, sodium hydroxide, potassium oxide, or potassium hydroxide, or a mixture of any two or more of the foregoing, and wherein the alcohol used in such reaction medium is predominantly or entirely an alkanol containing up to about 4 carbon atoms in the molecule or a mixture of any two or more of such alkanols.

33. A process as claimed in claim 31 wherein said substance used in such treatment consists essentially of sodium sulfide or potassium sulfide or a mixture of the foregoing, and wherein the alcohol used in such reaction medium is predominantly or entirely an alkanol containing up to about 4 carbon atoms in the molecule or a mixture of any two or more of such alkanols.

* * * * *